US009084773B2

(12) United States Patent
Bassler et al.

(10) Patent No.: US 9,084,773 B2
(45) Date of Patent: *Jul. 21, 2015

(54) SMALL MOLECULE ANTAGONISTS OF BACTERIAL QUORUM-SENSING RECEPTORS

(71) Applicant: The Trustees of Princeton University, Princeton, NJ (US)

(72) Inventors: Bonnie L. Bassler, Princeton, NJ (US); Lee R. Swem, Montara, CA (US); Scott M. Ulrich, Ithaca, NY (US); Colleen T. O'Loughlin, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/288,984

(22) Filed: May 28, 2014

(65) Prior Publication Data

US 2014/0275232 A1   Sep. 18, 2014

Related U.S. Application Data

(63) Continuation of application No. 13/550,961, filed on Jul. 17, 2012, now Pat. No. 8,772,331, which is a continuation of application No. 12/643,574, filed on Dec. 21, 2009, now Pat. No. 8,247,443.

(60) Provisional application No. 61/203,371, filed on Dec. 22, 2008, provisional application No. 61/270,979, filed on Jul. 15, 2009.

(51) Int. Cl.
| *A61K 31/381* | (2006.01) |
| *C07D 333/32* | (2006.01) |
| *A61K 31/365* | (2006.01) |
| *A01N 43/08* | (2006.01) |
| *A01N 43/10* | (2006.01) |
| *A01N 43/16* | (2006.01) |
| *A01N 43/18* | (2006.01) |
| *A61K 31/341* | (2006.01) |
| *C07D 307/33* | (2006.01) |
| *C07D 333/36* | (2006.01) |

(52) U.S. Cl.
CPC .............. *A61K 31/365* (2013.01); *A01N 43/08* (2013.01); *A01N 43/10* (2013.01); *A01N 43/16* (2013.01); *A01N 43/18* (2013.01); *A61K 31/341* (2013.01); *A61K 31/381* (2013.01); *C07D 307/33* (2013.01); *C07D 333/36* (2013.01)

(58) Field of Classification Search
None
See application file for complete search history.

(56) References Cited

U.S. PATENT DOCUMENTS 8,247,443 B2 *  8/2012  Bassler et al. ................ 514/445

OTHER PUBLICATIONS

Bassler Bonnie L. et al.; Intercellular signalling in Vibrio harveyi: sequence and function of genes regulating expression of luminescence ;Molecular Microbiology (1993) 9(4) 773-786.
Bassler Bonnie L. et al.; Multiple signalling systems controlling expression of luminescence in *Vibrio harveyi*: sequence and function of genes encoding a second sensory pathway; Molecular Microbiology (1994) 13(2); 273-86.
Freeman, Jeremy A., et al.; A genetic analysis of the functions of LuxN: a two-component hybrid sensor kinase that regulates quorum sensing in *Vibrio harveyi*; Molecular Microbiology (2000) 35(1); 139-49.
Fuqua, W. Claiborne, et al.; Quorum Sensing in Bacteria: the LuxR-LuxI Family of Cell Density-Responsive Transcriptional Regulators; Journal of Bacteriology, Jan. 1994; vol. 176; No. 2; p. 269-275.
Furste, Jens P., et al.; Molecular cloning of the plasmid RP4 primase region in a multi-host-rangetacP expression vector; Gene. 48 (1986) 119-131.
Jung, Kirsten, et al.; The Quorum-Sensing Hybrid Histidine Kinase LuxN of *Vibrio harveyi* Contains a Periplasmically Located N Terminus; Journal of Bacteriology, Apr. 2007; vol. 189; No. 7; p. 2945-2948.
Minogue, Timothy D., et al.; The autoregulatory role of EsaR, a quorum-sensing: regulator in *Pantoea stewartii* ssp. *stewartii*: evidence for a repressor function; Molecular Microbiology; (2002) 44(6); 1625-1635.
Minogue, Timothy D., et al.; The cell density-dependent expression of stewartan exopolysaccharide in *Pantoea stewartii* ssp. *stewartii* is a function of EsaR-mediated repression of the rcsA gene; Molecular Microbiology; (2005) 56 (1); 189-203.
Rumbaugh, Kendra P., et al.; Contribution of Quorum Sensing to the Virulence of *Pseudomonas aeruginosa* in Burn Wound Infections; Infection and Immunity; Nov. 1999; vol. 67; No. 11; p. 5854-5862.
Sjoblom, Solveig, et al.; Cooperation of two distinct ExpR regulators controls quorum sensing specificity and virulence in the plant pathogen *Erwinia carotovora*; Molecular Microbiology; (2006) 60(6), 1474-1489.

(Continued)

*Primary Examiner* — Jason Sims
*Assistant Examiner* — Tori M Strong
(74) *Attorney, Agent, or Firm* — Meagher Emanuel Laks Goldberg & Liao, LLP

(57) ABSTRACT

A novel small molecule antagonizes two types of acyl homoserine lactone receptors: membrane-bound and cytoplasmic. A focused library of analogs and derivatives of the original antagonist was synthesized. Analog and derivative molecules harbor a range of activities. The novel small molecule and most potent antagonist protects the eukaryote *Caenorhabditis elegans* from quorum-sensing-mediated killing by the bacterial pathogen *Chromobacterium violaceum*. The saving of *C. elegans* demonstrates the use of these molecules as small molecule antimicrobials.

10 Claims, 12 Drawing Sheets

(56) References Cited

OTHER PUBLICATIONS

Stieritz, Donald D., et at.; Experimental Studies of the Pathogenesis of Infections Due to *Pseudomonas aeruginosa*: Description of a Burned Mouse Model; The Journal of Infectious Diseases, vol. 131; No. 6 (Jun. 1975); pp. 688-691.

Swem, Leer., et al.; Deducing receptor signaling parameters from in vivo analysis: LuxN/AI-1 quorum sensing in *Vibrio harveyi*; Cell. Aug. 8, 2008; 13 (3); 461-473.

Timmen, Melanie, et al.; AI-1 Influences the Kinase Activity but Not the Phosphatase Activity of LuxN of *Vibrio harveyi*; J. Biol. Chem.; (2006); 281; 24398-24404.

Zhang, Rong-Guang, et al.; Structure of a bacterial quorum-sensing transcription factor complexed with pheromone and DNA; Nature; vol. 417; Jun. 27, 2002; 971-974.

Zhu, Jun et al.; Autoinducer binding by the quorum-sensing regulator TraR increases affinity for target promoters in vitro and decreases TraR turnover rates in whole cells; Proc. Nail. Acad. Sci USA; Apr. 1999; vol. 96; pp. 4832-4837.

Zhu, Jun et al.; The quorum-sensing transcriptional regulator TraR requires its cognate signaling ligand for protein folding, protease resistance, and dimerization; PNAS; Feb. 13, 2001; vol. 98; No. 4; 1507-1512.

Throup, J. et al.; Signalling in Bacteria Beyond Luminescence. In Bioluminescence and Chemiluminescence: Fundamentals and Applied Aspects; L.K. A. Campbell & P. Stanley. ed; (Chichester: Wiley, 1995; pp. 89-92.

\* cited by examiner

US 9,084,773 B2

SMALL MOLECULE ANTAGONISTS OF BACTERIAL QUORUM-SENSING RECEPTORS

CROSS-REFERENCE TO RELATED APPLICATIONS

This application claims priority to U.S. Provisional Application No. 61/203,371, filed Dec. 22, 2008, U.S. Provisional Application No. 61/270,979, filed Jul. 15, 2009, PCT Application No. PCT/US2009/003348, filed Jun. 2, 2009, filed nationally on Dec. 21, 2009 as U.S. patent application Ser. No. 12/643,574, which issued on Aug. 21, 2012 as U.S. Pat. No. 8,247,443, and U.S. patent application Ser. No. 13/550,961, filed on Jul. 17, 2012, all of which are herein incorporated by reference in their entirety.

STATEMENT OF GOVERNMENT INTEREST

This invention was made with Government support under Grants #2 R01 GM065859 and #5 F32 GM078755 awarded by the National Institutes of Health and Grants #MCB-0639855 and #MCB-0343821 awarded by the National Science Foundation. The Government has certain rights in the invention.

BACKGROUND OF THE INVENTION

In a process referred to as quorum sensing, bacteria communicate using chemical signal molecules called autoinducers. By monitoring increases and decreases in autoinducer concentration, quorum-sensing bacteria track changes in cell-population density and synchronously switch into and out of group behaviors. Quorum sensing allows bacteria to collectively carry out tasks that would be unsuccessful if carried out by an individual bacterium acting alone.

Gram-negative quorum-sensing bacteria typically employ acyl homoserine lactones (AHLs) as autoinducers and each bacterial species detects the cell-density-dependent accumulation of one or more particular AHL molecule(s). AHL detection occurs by one of two distinct mechanisms.

In the first mechanism, cytoplasmic LuxR-type proteins detect AHLs that diffuse into the cell (FIG. 1A)(Fuqua et al., 1994). In these cases, the unliganded LuxR-type proteins are insoluble and degraded at low cell density (LCD) when AHL concentrations are low (Zhu and Winans, 1999, 2001). At high cell density (HCD), when AHLs are present, AHL binding to the cognate LuxR-type proteins promotes folding of the LuxR-type protein-AHL complexes. The complexes bind DNA and activate quorum-sensing target genes (Zhang et al, 2002). However, there are a few cases in which the LuxR-type proteins fold, bind DNA, and repress target gene transcription in the absence of AHL (Minogue et al., 2002, 2005; Sjoblom et al., 2006). In these cases, accumulation and binding of AHL relieves repression and this depends on the location of the DNA binding site, rather than on some unique structural feature of the receptor. *Chromobacterium violaceum* provides an example of this first mechanism, with the AHL being C6-homoserine lactone (HSL), the LuxR-type protein being CviR, and the target genes being vio genes, which are involved in production of violacein protein.

In the second mechanism, AHLs are detected by membrane-bound two component histidine kinase-type proteins of the LuxN family (FIG. 1B) (Freeman et al., 2000; Jung et al., 2007; Swem et al., 2008; Timmen et al., 2006). In these cases, accumulated AHLs are detected outside the cell (e.g. in the periplasm) and AHL binding by the cognate LuxN receptor elicits a change in its auto-phosphorylation and phosphotransfer activities. These complexes relay information internally by phosphorylation cascades that impinge on downstream DNA binding proteins that are responsible for directing gene expression changes. This causes a change in the phosphorylation state of a downstream DNA binding transcription factor, which alters its activity and promotes the quorum-sensing gene expression response.

Infectious bacteria, which include human, animal, plant, and marine pathogens, use AHL quorum sensing strategies to control virulence. Typically, bacterial infections are treated with bactericidal or bacteriostatic molecules that impede four major processes: DNA replication, transcription, translation or tetrahydrofolic acid synthesis. Existing methods for treating bacterial infection unfortunately exacerbate the growing antibiotic resistance problem because they inherently select for growth of bacteria that in turn can resist the drug. What is needed are new treatments that avoid selecting for drug resistant bacteria.

It is well established that quorum sensing plays a fundamental role in bacterial pathogenicity in both Gram-positive and Gram-negative bacteria. However, previous attempts to inhibit AHL-mediated quorum sensing in Gram-negative bacteria have not provided promising results in vivo.

The bacterium *Pseudomonas aeruginosa* is the major pathogen associated with cystic fibrosis lung infection, keratitis eye infection, and third-degree burn-associated skin infections. There are *P. aeruginosa* mutant strains that lack the AHL synthase and thus do not produce endogenous autoinducer. Molecules have been studied in vitro that inhibit LasR, a receptor for the AHL. However, those studies on *P. aeruginosa* have not included in vivo testing on wild type bacteria.

Quorum sensing also controls biofilm formation. Biofilms are communities of bacterial cells adhered to surfaces and are highly problematic, for example in industrial processes (e.g., clogging of cooling towers in manufacturing plants) and in hospital or other clinical settings (e.g., catheter and implant infections). Initial studies with *Staphylococcus aureus* and *Staphylococcus epidermidis* indicated that manipulation of a form of quorum sensing that is peptide-mediated would not have successful results. Most notably, disruption of the peptide quorum-sensing circuit in *S. epidermidis* by deleting necessary quorum sensing genes led unexpectedly to increased biofilm formation on implanted medical devices. Therefore what is needed are new treatments for bacterial infection that can more subtly manipulate bacterial behaviors that promote health problems.

SUMMARY OF THE INVENTION

Quorum sensing controls virulence factor production in many clinically relevant bacteria. Thus, methods described herein that disrupt quorum sensing are useful health treatment alternatives to administering traditional antibiotics. Interference with either the production or the detection of autoinducer molecules can abolish bacterial communication and render bacteria non-pathogenic. Methods that disrupt quorum sensing are also useful in dealing with problematic bacterial biofilms. The present invention identifies novel small molecules that can be used to positively and negatively manipulate quorum-sensing-mediated communication to control bacterial quorum sensing-dependent behaviors.

Accordingly, in a first aspect, the invention features a small molecule compound characterized by its ability to bind to *Vibrio harveyi* LuxN at the autoinducer-1 (AI-1) binding site of LuxN, wherein the compound is an analog of 4-(4-chloro- 2-methylphenoxy)-N-(2-oxotetrahydrothiophen-3-yl)butanamide (compound 4606-4237). Embodiments of the invention include various isolated and purified analogs of compound 4606-4237. In a preferred embodiment, the compound is one of the small molecules from the group consisting of the structures shown in FIG. 9.

In another aspect, the invention features a *V. harveyi*-LuxN antagonist compound that is one of the analog compounds of the invention. In one embodiment the analog is selected from the group consisting of the structures shown in FIG. 9.

In a related aspect, the invention features a method of disrupting detection of acyl-homoserine lactone autoinducer in Gram-negative bacteria comprising contacting the bacteria with an inventive small molecule compound of the invention.

In another related aspect, the invention features a pharmaceutical composition comprising a pharmaceutically acceptable carrier, excipient or diluent and one or more of the inventive small molecule compounds. In one embodiment, the compound is selected from the group consisting of the structures shown in FIG. 9.

In a further related aspect, the invention features a method of inhibiting bacterial infection of a host comprising contacting the bacteria with the inventive pharmaceutical composition, wherein the bacteria are Gram-negative quorum sensing bacteria.

In yet another related aspect, the invention features a bacterial biofilm-inhibiting composition comprising one or more of the inventive compounds. A preferred embodiment provides a compound selected from the group consisting of the structures shown in FIG. 9. In a preferred embodiment the composition also comprises DMSO.

In still another related aspect, the invention features a method of controlling growth of quorum sensing Gram-negative bacteria attached to a solid surface, comprising exposing the bacteria to the bacterial biofilm-inhibiting composition.

A related aspect of the invention features a method of preventing biofilm formation on a solid surface comprising administering the bacterial biofilm-inhibiting composition to the surface.

Another aspect of the invention features a method of inhibiting quorum sensing-mediated activity in Gram-negative bacteria comprising contacting the bacteria with the inventive antagonist compound, preferably the compound selected from the group consisting of the structures shown in FIG. 9.

In a preferred embodiment the quorum sensing-mediated activity is pathogenicity. In another preferred embodiment the bacteria are pathogenic to humans, animals, plants or marine life. In a particularly preferred embodiment the activity is pathogenicity and the bacterial species is selected from *V. harveyi* and *C. violaceum*.

In another preferred embodiment, the activity is bioluminescence, siderophore production, type III secretion, or metalloprotease production.

Additional features and advantages of the present invention will be better understood by reference to the drawings, detailed description and examples that follow.

DETAILED DESCRIPTION OF THE INVENTION

Figure 2:
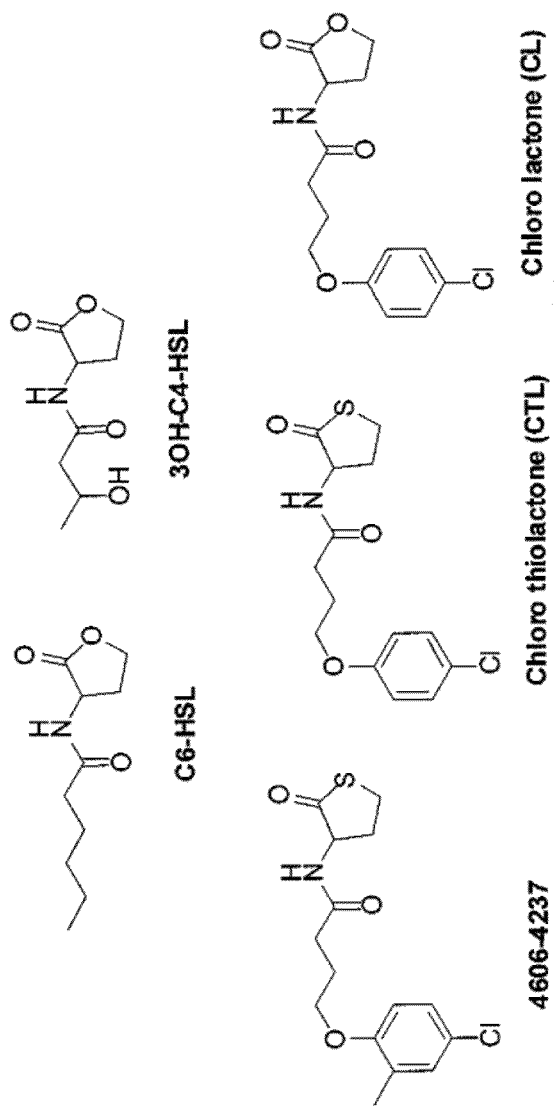
FIG. 2. Structures of the Quorum-Sensing Autoinducers and Synthetic Antagonists. Structures and designations of the quorum-sensing autoinducers and synthetic antagonists for *C. violaceum* and *V. harveyi*.

One aspect of the invention is directed to a class of HSL antagonist molecules that have the unique ability to antagonize two different quorum-sensing receptor types. Specifically, the antagonists inhibit both the membrane bound sensor kinase, LuxN and the cytoplasmic transcriptional regulator, CviR. Remarkably, the core features of the antagonists are equally important for potent activity against both receptor types. This finding is particularly surprising because LuxN and CviR are not evolutionarily conserved proteins although both receptors bind and respond to similar ligands, namely, LuxN binds 3OH-C4-HSL and CviR binds C6-HSL (FIG. 2).

In the quorum-sensing bacterium, *Vibrio harveyi*, the strongest autoinducer signal is the AHL 3OH-C4-HSL (FIG. 2) and it is detected by LuxN, the defining member of the family of membrane-bound two-component AHL receptor proteins. LuxN-type and LuxR-type AHL receptors have no obvious sequence homology and they employ distinct mechanisms for signal transduction. However, each type of receptor must bind an AHL and AHLs share common structural features. The experiments described below were designed to determine if LuxR-type and LuxN-type receptors have structurally similar AHL binding pockets. The experiments indicate that this is the case and thus led to the inference that the molecules that antagonize a LuxN-type receptor and compete for the AHL binding site, would reasonably also antagonize a LuxR-type AHL receptor. The binding activities of the antagonist molecules of the present invention support this inference.

Initial high-throughput chemical library screens allowed for the identification of small molecules that disrupt detection of acyl-homoserine lactone-type autoinducers in Gram-negative bacteria and thus are identified as antagonists of LuxN. (FIG. 8A). One strong antagonist was studied in detail. This was 4-(4-chloro-2-methylphenoxy)-N-(2-oxotetrahydrothiophen-3-yl)butanamide (compound 4606-4237) (FIG. 2). Characterization revealed that the antagonist competes for the AHL binding site of LuxN and also strongly antagonizes a canonical LuxR-type protein called CviR from *Chromobacterium violaceum*.

As used herein, a LuxR-type protein is a transcriptional regulatory protein that binds directly to an acylated homoserine lactone molecule and then dimerizes. This dimer then binds directly to a DNA promoter element and either activates or represses transcription of downstream genes.

Based on the initially identified antagonist 4606-4237, a set of related molecules was synthesized and tested for antagonist activity against CviR. Some of the molecules had no activity. Molecules that possessed antagonist activity functioned by two different mechanisms. The first mechanism can be represented by the example of C8-HSL and C10-HSL. In this case, CviR is highly sensitive to C8-HSL, but only half-maximal green fluorescent protein (gfp) production is induced by this molecule. Gel mobility shift analyses indicate that the decreased gfp expression is not due to disruption of DNA binding. Therefore, the results can be taken to indicate that C8-HSL places the CviR receptor into a conformation that binds DNA but does not engage in all of the same interactions with RNA polymerase as does the CviR receptor bound to the native ligand, C6-HSL. Extending the acyl-chain by two additional carbons (C10-HSL) further exacerbates the problem. In this case, CviR binds DNA equally well as when bound to C6-HSL or C8-HSL, but the CviR C10-HSL complex apparently cannot make the contacts with RNA polymerase necessary to activate transcription.

The second mechanism of CviR antagonism is typified by disruption of DNA binding. In these cases (as represented by C12-HSL, C14-HSL, 4606-4237, Chloro-thiolactone (CTL) or chlorolactone (CL), for example), the antagonists bind and solubilize the CviR receptor, but do not allow the protein to adopt a conformation suitable for DNA binding. These results indicate that the activity of LuxR-type receptors are modulated by partial antagonists that function like C8-HSL in order to fine-tune their respective quorum-sensing outputs. In scenarios where complete abrogation of quorum-sensing behaviors is desired, more potent antagonists (i.e., C12-HSL, 4606-4237, etc.) can be employed.

Because the strong antagonists of the present invention also eliminate the LuxN response to its cognate AHL signal, it is not a prerequisite that the particular targeted-quorum-sensing receptor binds DNA or interacts with RNA polymerase for successful antagonism by the above class of molecules. In the case of LuxN, the antagonists presumably function by binding to the periplasmic domain. The analyses described herein suggest that the antagonists act as competitive inhibitors for LuxN binding to the native signal which binds in the periplasm. Irrespective of where the molecules bind to LuxN, what is clear is that they act to prevent LuxN from switching from kinase-mode to phosphatase-mode, and in so doing, they prevent autoinducer reception.

Figure 8:
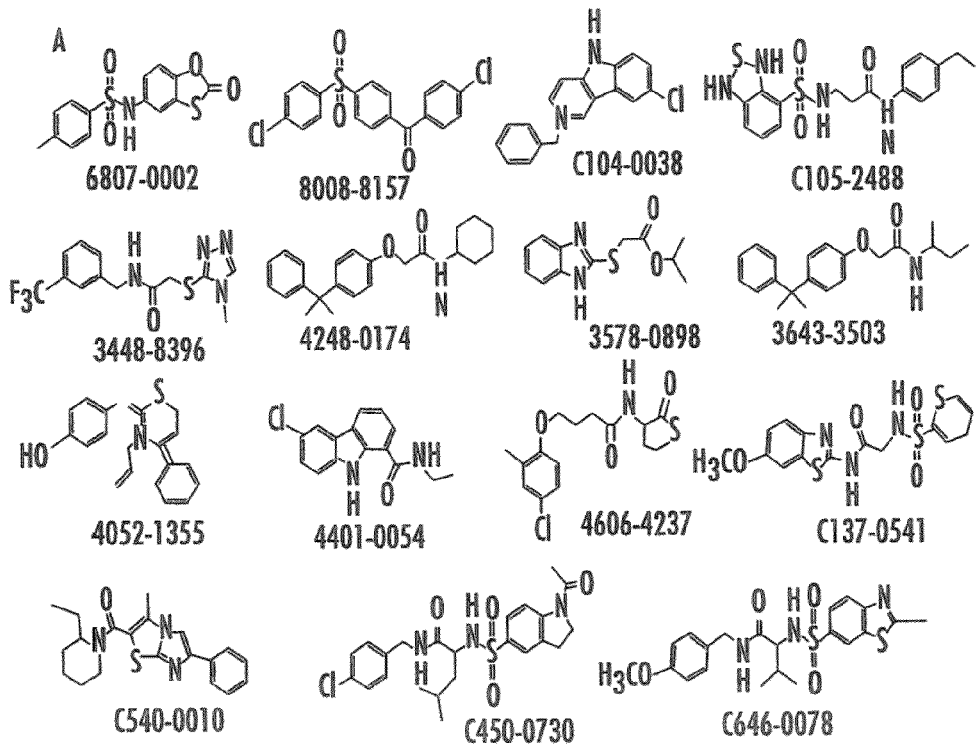
FIG. 8. Structures of 15 LuxN Antagonist Molecules and Their Effects on Violacein Production. (A) Structures and designations of the 15 identified LuxN antagonists. All molecules were purchased from Chemdiv. (B) The *C. violaceum* cviI-mutant was grown in the presence of no HSL (first bar), 5 µM exogenously supplied C6-HSL (second bar), or 5 µM exogenous C6-HSL and 50 µM of each antagonist (remaining bars). Violacein was methanol extracted and quantified by measuring the absorbance at 568 nm.
Figure 8:
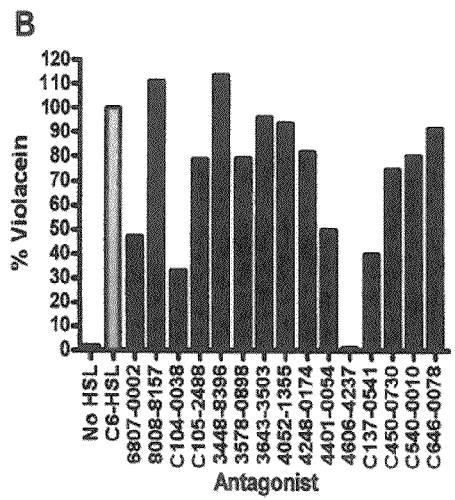

The set of molecules that was synthesized are based on the core structure of the potent LuxN and CviR antagonist which is compound 4606-4237 (FIG. 8). A generalized formula for the synthesized molecules of the present invention is:

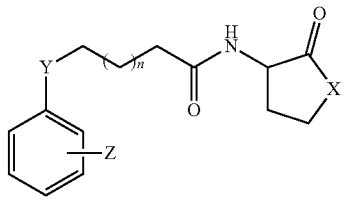

wherein X is O or S (preferably O); n is 0, 1 or 2 (preferably 1); Y is O, S or CH$_2$ (preferably O);

wherein the aryl ring can be substituted (represented by Z) with halogens (preferably chlorine, bromine, or fluorine), hydroxyl, alkoxyl (wherein the alkyl group is preferably methyl, ethyl, propyl, or isopropyl), cyano, nitro, amido, acetamido, amino, alkylamino (wherein the alkyl group is preferably methyl, ethyl, propyl, or isopropyl), aryl, heteroaryl, acyl (wherein the acyl chain is preferably methyl, ethyl, propyl, or isopropyl), alkyl (wherein the alkyl group is preferably methyl, ethyl, propyl, or isopropyl), cycloalkyl (wherein the alkyl group is preferably propyl, butyl, pentyl, or hexyl), sulfonamide, alkyl sulfonamide (wherein the alkyl group is preferably methyl, ethyl, propyl, or isopropyl); wherein the aryl ring substituent Z can occur at the ortho, meta or para position; or wherein the aryl ring can be multiply substituted with the substituents as described above.

A preferred aryl substitution pattern is disubstitution with fluorine at the ortho position and chlorine at the para position.

The methods for synthesis of molecules in the library described above are exemplified by the following formula for synthesis of the chlorolactone:

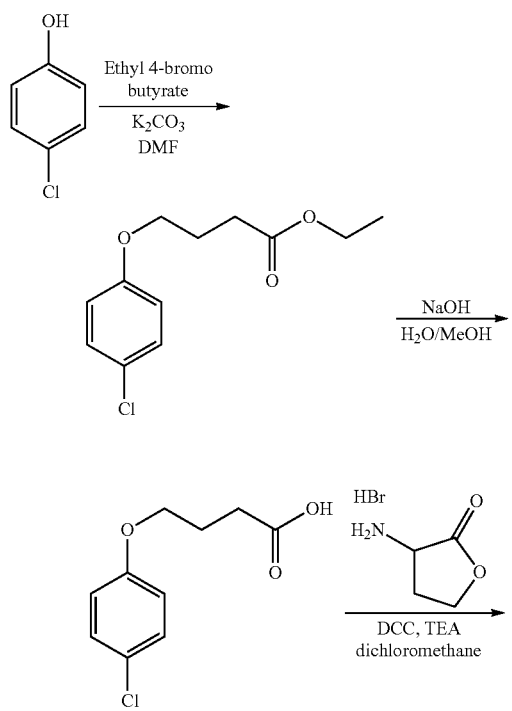

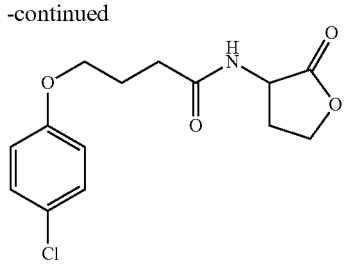

From the synthesized library, additional antagonists of the ligands of the autoinducers were identified, some with reduced and some with increased (10-100-fold) potency. The antagonists function by two mechanisms. One class of antagonists promotes CviR folding but prevents DNA binding. A second set of antagonists promote CviR folding and DNA binding but reduces or eliminates transcriptional activation suggesting that the CviR-antagonist complex cannot productively interact with RNA polymerase. The most potent CviR antagonist also functions as the strongest antagonist of LuxN, which is consistent with the original hypothesis that AHL-binding pockets are similar in these diverse receptors. This antagonist prevents *C. violaceum* killing of *C. elegans* by specifically inhibiting the CviR-dependent quorum-sensing virulence pathway.

Thus, many of the synthesized small molecules inhibit quorum sensing in bacteria and protect from quorum sensing-mediated bacterial pathogenesis of eukaryotes. These synthesized molecules work as anti-bacterial treatments through a novel molecular mechanism that interferes with quorum sensing.

In total, the antagonists identified here can serve as broad spectrum lead compounds for disrupting quorum sensing in pathogenic Gram-negative bacteria. Targeting quorum sensing (or other bacterial behaviors) provides the opportunity to potentially minimize, or at least delay the development of bacterial resistance, since these types of therapies interfere only with signaling and not growth. In essence, an anti-quorum-sensing therapy disables bacterial counting mechanisms causing bacteria to act as individuals in the host even when they have achieved sufficient numbers to initiate a successful virulence cascade, preventing the bacteria from gaining a toe-hold on the host. In so doing, anti-quorum-sensing drugs provide the host's immune system the needed time to ferret-out and eliminate the pathogen. Consistent with this, mutant analyses described herein convincingly demonstrated that clinically relevant pathogens lacking quorum sensing are attenuated for virulence. Such bacteria do not grow unchecked in model host organisms even though their repertoire of canonical virulence factors remain intact and only quorum-sensing-mediated communication is eliminated. The model system demonstrated herein shows that interfering with this vital "command-and-control" system is sufficient to fully cripple invading bacteria.

In our conceptualization of this new therapy, the bacterial quorum-sensing receptors work in a manner similar to eukaryotic G protein-coupled receptors. For example, extensive treatments of eukaryotic diseases have been developed with a variety of therapeutics that specifically target signaling and behavior, but not cell growth. Nearly half of all modern drugs interfere with G protein-coupled receptor signal transduction cascades and these therapies are currently used in the treatment of schizophrenia, general allergies, irritable bowel syndrome and acid reflux disease. Importantly, therapies have already successfully targeted G protein-coupled receptors in the treatment of multiple diseases.

The studies herein focus on strategies for interfering with bacterial quorum sensing in order to develop novel antimicrobial therapeutics. Most of the antagonist molecules identified herein are based on the core structure of the most potent AHL antagonist from a chemical library screen. The most potent of molecules tested herein were the 4-(4-chloro-2-methylphenoxy)-N-(2-oxotetrahydrothiophen-3-yl)butanamide (compound 4606-4237), Chloro-thiolactone (CTL) and chlorolactone (CL) molecules. In a similar manner, studies of Pseudomonas aeruginosa have elucidated molecules that contain a homoserine lactone head group with various acyl chain decorations that inhibit an AHL receptor, LasR. Some of these molecules appear to function in a similar manner to the 4606-4237, CTL and CL molecules presented here. It is intended that the molecules presented herein as bacterial antagonists and tested in model systems to establish antagonist activity, function in diverse quorum sensing bacterial species that share the common control mechanism.

Our results, most notably with the CL molecule, make the strong case and provide the first compelling in vivo evidence that an anti-quorum-sensing strategy is a valid alternative to traditional antibiotics for Gram-negative bacteria, and that there is merit to pursuing the clinical relevance of such strategies. Specifically, we successfully administered our strongest quorum-sensing antagonists in a model setting and showed that they improve the outcome of a wild type bacterial infection in an animal host, in this case, in the nematode C. elegans. The results of DNA binding analysis of ligand-bound-CviR to vioA promoter (FIG. 5B), showing that the strongest antagonist can exchange with the native autoinducer, provide evidence that quorum-sensing controlled virulent processes can indeed be reversed. Together, the biochemical and animal studies suggest that anti-quorum-sensing strategies hold promise as novel non-bactericidal, non-bacteriostatic drug therapies to treat Gram-negative and Gram-positive infections. Our finding that at least the CL antagonist molecule is potent enough to protect the animal from wild type virulent bacteria, suggests that quorum-sensing receptors are promising targets for drug development and furthermore, that small molecule antagonists can be identified and synthesized with relative ease.

The experiments described herein, which demonstrate inhibition of two autoinducer receptors that function by drastically different mechanisms, allowed us to conceptualize a similar mechanism for the ubiquitous AI-2 quorum sensing circuit. To elaborate, the gene encoding the AI-2 synthase, luxS, is found in over 50% of all sequenced prokaryotic genomes and disruption of AI-2 quorum sensing in pathogenic bacteria often leads to decreased virulence factor production. Two representative quorum sensing receptors for AI-2 have been identified as LuxPQ from V. harveyi and LsrB from Salmonella typhimurium. The present studies have allowed us to conceptualize identifying an AI-2 antagonist molecule that has the ability to target many different AI-2 receptor types, independent of the mode of action of the receptor.

The following examples set forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., Molecular Cloning, Cold Spring Harbor Laboratory (1989) (hereinafter "Sambrook et al.") or Ausubel et al. (eds) Current Protocols in Molecular Biology, John Wiley & Sons (1998) (hereinafter "Ausubel et al.") are used.

Experimental Procedures

Strains and Media.

Wild type C. violaceum strain ATCC31532 was purchased from the ATCC. The cviI mutant strain, CV026 was kindly supplied by Clay Fuqua and Paul Williams. C. violaceum strains were grown aerobically at 30° C. in either Luria-Bertani broth or Nutrient Broth supplemented with 1 mM trypotophan. V. harveyi strains were grown aerobically at 30° C. in autoinducer bioassay (AB) broth. AI-1 dose-response curves were generated in V. harveyi strains BB120, BB960 and JMH624 as described. E. coli was grown at 37° C. in Luria Bertani broth. The plasmid pET23b (Novagen) was used for expressing cviR in E. coli strain BL21-Gold (DE3) or BL21(DE3) pLysS (Stratagene) and maintained by inclusion of Ampicillin at 100 μg/ml. Plasmid pEVS141 was used for the vioA-gfp promoter fusion and maintained with 50 μg/ml of Kanamycin. A list of strains and plasmids used in this study is provided in the Table 1. C. elegans wild type strain, N2 was used for all of the nematode infection studies. Worms were propagated on Nematode Growth Media (NGM) medium with an E. coli OP50 lawn as the food source and allowed to multiply at 20° C.

TABLE 1

| Strain | Relevant feature | Reference or Source |
|---|---|---|
| BB120 | Wild type V. harveyi | (Bassler et al., 1993) |
| BB960 | luxQ::Tn5 | (Bassler et al., 1994) |
| JMH624 | ΔluxM, luxQ::Tn5 | unpublished |
| ATCC31532 | Wild type C. violaceum | ATCC database |
| CV026 | cviI::Tn5 | Throup et al., 1995 |
| ELS1257 | pET23/cviR and pvioA-gfp | this study |
| pJAK16 | multi-host-range tacP expression vector | Furste (Gene) 1986 | vioA-gfp Construction.

The vioA-gfp promoter fusion was constructed by amplifying the vioA promoter and cloning this region upstream of gfp in pEVS141 at the SphI and SalI sites. Cells containing the vioA-gfp construct were electroporated with the pET23 carrying cviR and selected on LB medium supplemented with 75 μg/mL ampicillin and 50 μg/mL kanamycin. The E. coli strain containing cviR and the vio:gfp reporter is named ELS 1257.

gfp and Violacein Dose-Response Analyses.

E. coli strains were grown overnight in LB medium with antibiotics at 37° C. and sub-cultured into fresh medium at a 1:100 dilution. Various AHL and antagonists were added at constant concentrations or titrated as stated. The gfp was measured on an Envision plate reader after 5 hours of growth at 37° C. C. violaceum strains were grown aerobically in 1 mL Nutrient Broth plus 1 mM tryptophan at 30° C. Cells were subcultured into 1 mL fresh medium at 1:1000 dilution, and the antagonist 4606-4237 or CL was tested at concentrations from 100 μM to 0.045 μM and CTL was titrated from 67 μM to 0.03 μM in cultures grown aerobically to steady state at 30° C. Cells were collected via centrifugation at 13000 rpm for 15 minutes. Pellets were resuspended in 1 mL of methanol and incubated at 42° C. for 1 hour. Samples were again collected via centrifugation at 13000 rpm for 5 minutes and analyzed for violacein by measuring optical density at 568 nm on a Beckman Coulter DU-800 spectrophotometer. For the dose-response analyses, all assays were performed in triplicate.

CviR Overexpression and Purification.

CviR was overexpressed in BL21(DE3) pLysS by growing an overnight culture in LB supplemented with 100 μg/mL ampicillin and 10 μg/mL chloramphenicol. The culture was diluted 1:50 into fresh LB supplemented with 100 μg/mL ampicillin and 10 μg/mL chloramphenicol and grown shaking at 37° C. to an $OD_{600}$ of 0.4. Various AHL or antagonist molecules were added to at 50 μM and incubated an additional 30 minutes at 30° C., after which expression was induced by the addition of 100 μM IPTG (isopropyl-β-D-thiogalactopyranoside) for 4 hours at 30° C. Cells were harvested by centrifugation and lysed in 20 mM imidazole pH 8.0, 100 mM NaCl, 0.5 mM EDTA and 5% glycerol via a Micro-fluidizer processor (MicroFluidics). Protein was purified via ion-exchange using a Hitrap Heparin HP column (GE Healthcare). Protein was eluted with a 100 mM to 1 M NaCl gradient. Fractions containing CviR were pooled and diluted in lysis buffer devoid of NaCl, and then further purified by cation exchange chromatography using a Hitrap SP HP column (GE Healthcare). CviR was eluted with a 100 mM to 1 M NaCl gradient. Fractions were pooled and 25% glycerol was added and protein was stored at −80° C.

Gel Mobility Shift Assays.

DNA probes for gel mobility shift analyses were generated by standard polymerase chain reaction using primers with a 5' 6-FAM (fluorescein) tag (Integrated DNA Technologies). The target probe contained about 100 nucleotides of the vioA promoter. The control probe contained 300 bases of vioB intergenic DNA. 37 ng of each probe was incubated for 20 minutes at room temperature with the indicated amounts of CviR (0, 0.1, 0.2, 0.3, 0.4 and 0.5 μM) and 1 μg/μL poly-dIdC in 1× Gel shift buffer (40 mM Tris HCl pH 8.0, 100 mM KCL, 2 mM EDTA, 2 mM DTT, 10% glycerol, 200 μg/mL BSA). Gel mobility shifts were performed on 6% TGE-polyacrylamide gels and visualized using a Storm 860 Imaging System (Molecular Dynamics).

Life Span Assays.

*C. elegans* lifespan assays were completed with at least 100 wild type N2 worms for each condition. *C. elegans* eggs were harvested from a large population of gravid adults using a standard bleaching protocol (30 mL 5% bleach, 15 mL N KOH, 55 mL $DH_2O$). Harvested eggs were placed on lawns of fresh *E. coli* OP50 and allowed to hatch and grow to the young adult (L4) stage before being moved onto lawns of *C. violaceum*. Worms were scored for survival each day and transferred to new *C. violaceum* lawns every two days until all worms had expired. C6-HSL, 4606-4237 and CL were added directly to NGM medium at 5 μM, 50 μM and 20 μM, respectively.

EXPERIMENTAL RESULTS

Example 1

Analyses of CviR Autoinducer Responses.

To assess LuxR-type AHL sensitivity and selectivity, *C. violaceum* strain ATCC31532 was employed. *C. violaceum* synthesizes and responds to C6-HSL (FIG. 2). The quorum-sensing readout for *C. violaceum* is the easily quantifiable purple pigment, violacein. Violacein production requires CviR binding to C6-HSL at high cell density and subsequent activation of transcription of the vioABCDE biosynthetic gene cluster that is responsible for violacein production. *C. violaceum* also possesses a repressor of vioABCDE. The repressor locus was identified and characterized (gene CV1055). This repressor is inactivated in the violacein assay strain.

Figure 3:
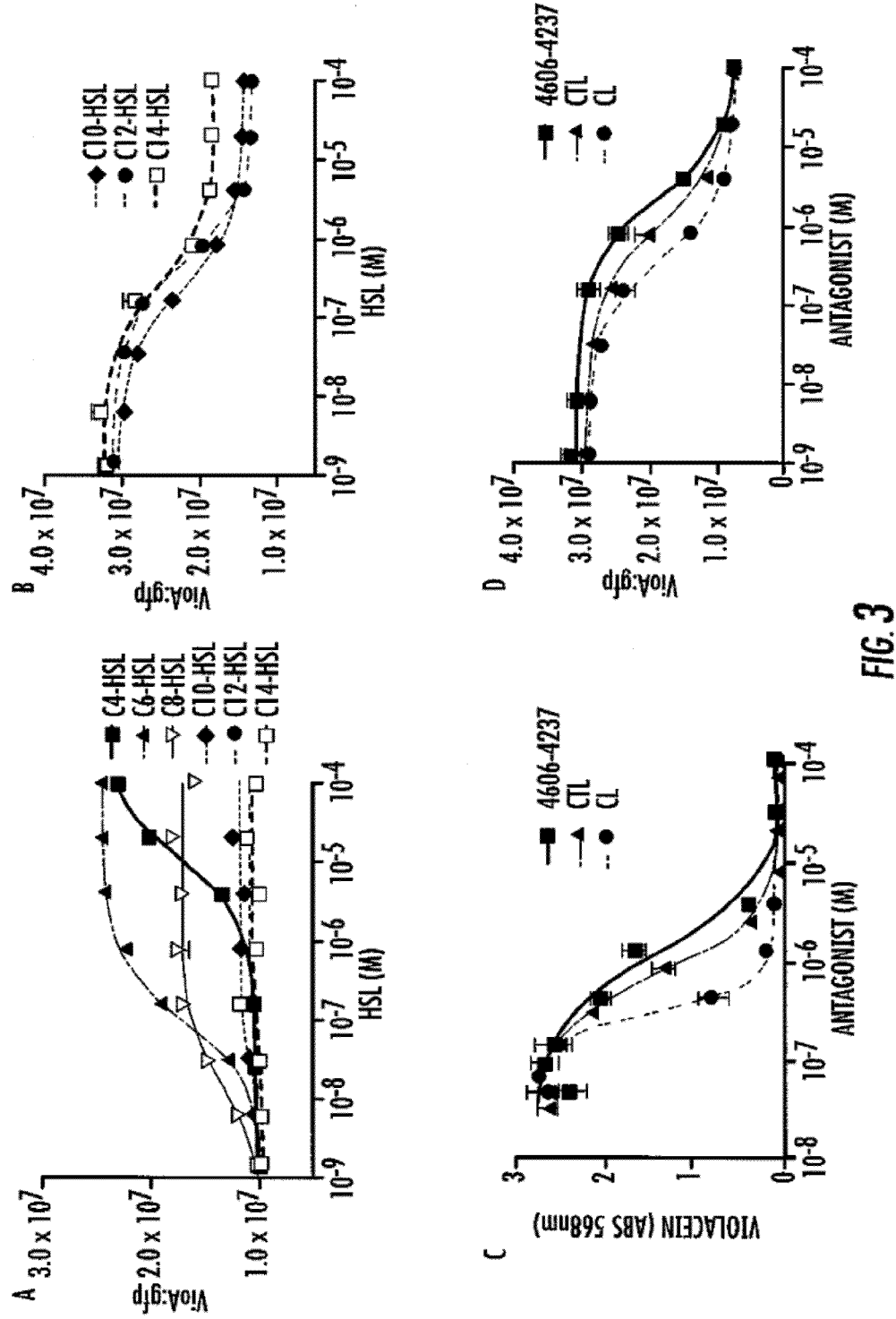
FIG. 3. CviR Dose-Response Curves. (A) CviR-dependent vioA-gfp expression in *E. coli* is plotted as a function of concentration of the specified homoserine lactone (HSL) molecules. (B) Inhibition of CviR-dependent vioA-gfp expression in *E. coli* is plotted as a function of the concentration of the specified molecule in the presence of a 500 nM C6-HSL. (C) CviR-dependent violacein production in wild type *C. violaceum* is plotted as a function of specified antagonist molecule. (D) Inhibition of CviR-dependent vioA-gfp expression in *E. coli* is plotted as a function of the specified antagonist molecule. In all panels, data were fit with a variable-slope sigmoidal dose-response curve to determine $EC_{50}$ or $IC_{50}$ values. Error bars represent the standard error of the mean for three independent trials.

To examine the specificity and sensitivity of CviR, an *E. coli* strain was engineered that expresses CviR and contains a plasmid harboring the vioA promoter fused to green fluorescent protein (gfp). Thus, the ability of CviR to activate transcription can be assessed by measuring gfp expression in the presence of various molecules. First tested was the CviR response to a variety of AHL molecules with varying acyl-tail lengths (FIG. 3A). CviR activates significant vioA-gfp expression in response to C4-HSL, C6-HSL (the native signal), and C8-HSL with $EC_{50}$ values of 12 μM, 75 nM, and 30 nM, respectively (FIG. 3A). Although C4-HSL can induce maximal vioA-gfp expression, it takes nearly three orders of magnitude more C4-HSL than C6-HSL to do so. The longer acyl-tail length AHL molecules, C10-HSL, C12-HSL, and C14-HSL do not induce vioA-gfp expression through CviR even at 100 μM. A curious finding regarding CviR is that it has a similar sensitivity for C6-HSL ($EC_{50}$=75 nM) and C8-HSL ($EC_{50}$=30 nM), yet the two molecules do not activate vioA-gfp expression to the same maximal level (FIG. 3A). Specifically, C8-HSL induces only half of the maximal vioA-gfp expression induced by C6-HSL. This result indicates that the C8-HSL autoinducer readily binds to CviR but induces a conformational change in the CviR protein that, while obviously not completely negating its interaction with RNA polymerase, decreases its transcriptional activating potential with respect to that of C6-HSL bound CviR.

Consistent with the long chain AHL molecules not inducing CviR transcriptional activation, C10-HSL, C12-HSL, and C14-HSL have been reported to antagonize the CviR protein. The $IC_{50}$ values for C10-HSL, C12-HSL, and C14-HSL in the presence of constant (500 nM) C6-HSL were measured to be 208 nM, 494 nM and 268 nM, respectively (FIG. 3B). The $IC_{50}$ values for these antagonist molecules are quite low, suggesting that the CviR receptor has similar binding affinity for the long acyl-tail length AHL molecules as it does for the native C6-HSL autoinducer. However, binding of the longer acyl-tail length AHL molecules disrupts the transcriptional activation ability of CviR.

Example 2

Identification of CviR Antagonists

High-throughput chemical library screens had identified 15 molecules that inhibit AHL detection by the membrane-bound two-component AHL receptor LuxN (structures are provided in FIG. 8A). Experiments were undertaken to establish whether any of these LuxN antagonist molecules could also interfere with AHL binding to CviR. To examine this, each of the 15 molecules was tested for inhibition of in vivo violacein production in *C. violaceum*. For this set of experiments, a *C. violaceum* cviI mutant that produces no endogenous AHL signal was used. The native C6-HSL signal was added exogenously and held constant at 5 μM and violacein production was measured in the presence of 50 μM of each potential antagonist (FIG. 8B). Importantly, because the cviI mutation in the *C. violaceum* test strain renders it incapable of AHL production, this strain does not produce violacein in the absence of exogenously supplied AHL (FIG. 8B, bar denoted No HSL). One of the LuxN antagonists (denoted 4606-4237) completely abolished violacein production when examined at 10-fold higher concentration than the native C6-HSL ligand. Importantly, molecule 4606-4237 does not inhibit bacterial growth.

Example 3

Characterization of the CviR Antagonist 4606-4237

To quantify the in vivo potency of 4606-4237, further characterization was undertaken of violacein production in wild type C. violaceum (i.e., the wild type strain carrying a functional cviI gene that produces native levels of C6-HSL) in response to 4606-4237 at concentrations ranging from 45 nM to 100 µM (FIG. 3C). The antagonist, 4606-4237 inhibits violacein production in C. violaceum with an $IC_{50}$ value of 1.2 µM (FIG. 3C). To determine if 4606-4237 inhibits violacein production specifically by interfering with CviR, 4606-4237 was tested for antagonism of CviR in the recombinant E. coli vioA-gfp assay. For these experiments, C6-HSL was held constant at 500 nM, while 4606-4237 was titrated from 1.3 nM to 100 µM (FIG. 3D). This concentration of native C6-HSL signal induces maximal gfp production in this heterologous assay system. Importantly, no C. violaceum components other than CviR are present in the recombinant E. coli assay strain. Thus, any inhibition occurring would be due to a specific interaction between the antagonist molecule 4606-4237 and CviR rather than an interaction of 4606-4237 with some unknown component required for violacein production in C. violaceum. Indeed, the 4606-4237 molecule strongly inhibited vioA-gfp expression with an $IC_{50}$ value of 2.2 µM, similar to what was determined for the in vivo inhibition activity (FIG. 3C). Thus, 4606-4237 functions by disabling CviR-mediated activation of gene expression in both the C. violaceum in vivo violacein assay and the recombinant E. coli vioA-gfp assay.

Example 4

Structure-Function Analysis of 4606-4237 and Derivatives

Figure 9:
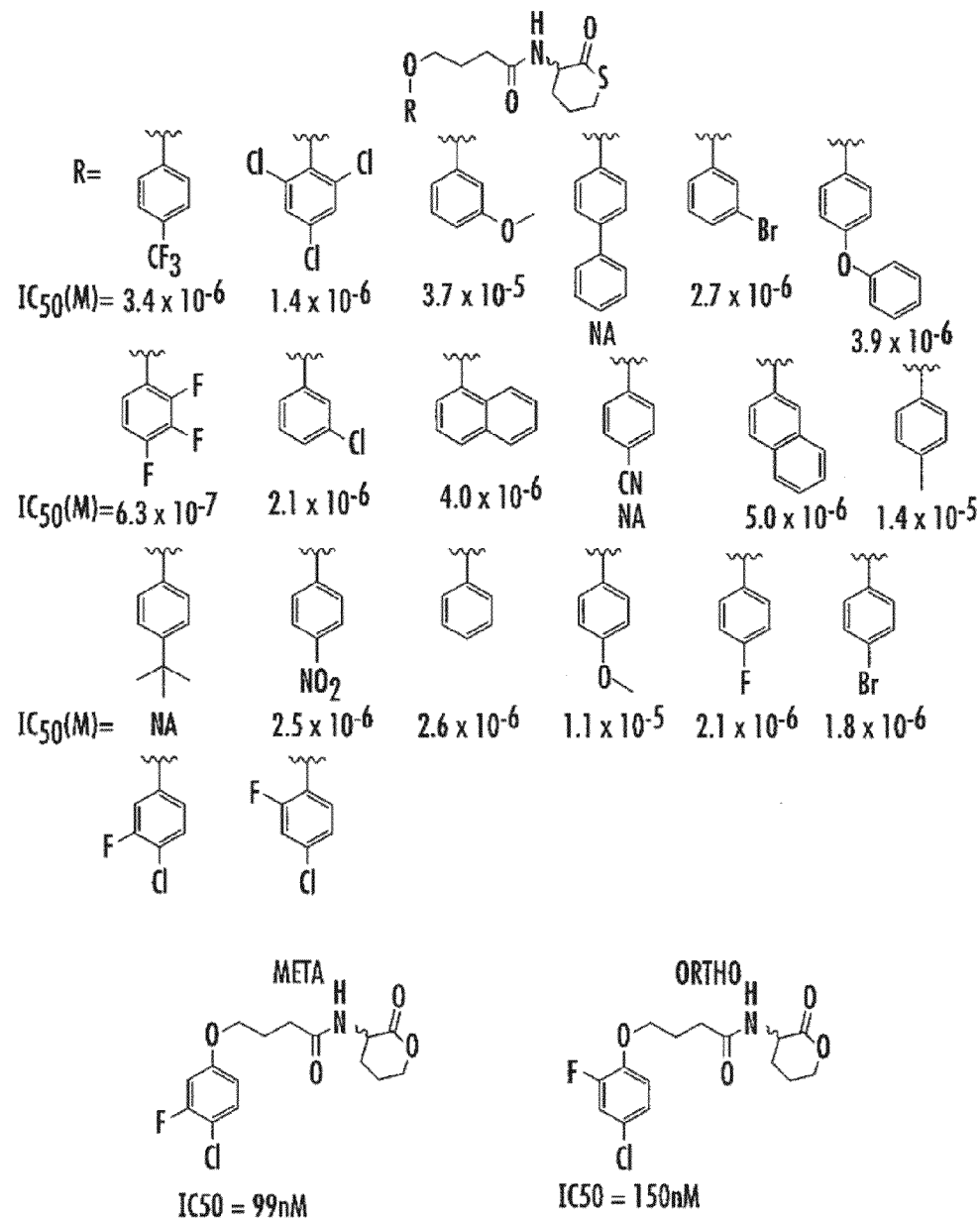
FIG. 9. Structures and Activities of 4606-4237 Molecule Derivatives. The core structure is shown as the topmost structure with R representing the position of the side group. Shown below the core structure are the possibilities for the side group R. The wavy line over each R group represents the core structure. The two structures at the bottom of the page are two alternative meta and ortho structures. The $IC_{50}$ or $EC_{50}$ values in the *E. coli* CviR-dependent vioA-gfp assay in the presence of each molecule were calculated from triplicate variable-slope sigmoidal dose-response curves and are listed below the structures in Molar (M) or Nanomolar (nM) units.

To explore the structural features of 4606-4237 critical for antagonism of CviR, a focused library of small molecules was synthesized, based on the core structure of 4606-4237. The structures and antagonist activities of all of the derivatives are supplied in FIG. 9. Analogous to the parent molecule 4606-4237, most of the derivatives were antagonists of CviR (FIG. 9). For example, moving the chlorine atom from the para to the meta position of the phenol ring did little to the antagonist activity against CviR ($IC_{50}$=2.1 µM). By contrast, addition of a fluorine atom to the ortho, meta, and para positions marginally increased the antagonistic activity ($IC_{50}$=630 nM). Incorporation of a ter-butyl or a phenol moiety at the para position eliminated antagonist activity. Cumulative analysis of the activities of this set of synthesized molecules revealed that placing a halogen atom at the para position of the phenyl along with elimination of the methyl moiety from the ortho position increased antagonism efficacy ($IC_{50}$ decreases from 2.2 µM to 1.1 µM; FIG. 2 and FIG. 3D denoted CTL). Replacing the sulfur with an oxygen atom in the thiolactone head group increased the potency of the antagonist nearly 10-fold over that of the original 4606-4237 molecule giving an $IC_{50}$ value of 377 nM (FIG. 2 and FIG. 3D denoted CL). Thus, CL is the strongest synthetic antagonist identified from this study. Similarly, analogs with the sulfur in the lactone ring replaced with an oxygen and with fluorine in the meta or ortho positions provided potent antagonists with IC50 values of approximately 100 nM.

The in vivo potency of CTL and CL were tested at concentrations ranging from 31 nM to 100 µM. Both CTL and CL inhibited in vivo violacein production in a dose-dependent manner with $IC_{50}$ values of 723 nM and 295 nM, respectively (FIG. 3C) Importantly, the efficacy of 4606-4237, CTL, and CL follow identical patterns in both the E. coli vioA-gfp assay and the in vivo C. violaceum violacein assay (FIGS. 3C and 3D). This result shows that, similar to the parent molecule 4606-4237, both CTL and CL traverse the E. coli and C. violaceum membranes and likely function by directly interfering with CviR-dependent transcriptional activation.

Example 5

CviR Protein-Antagonist Binding Analysis

Figure 4:
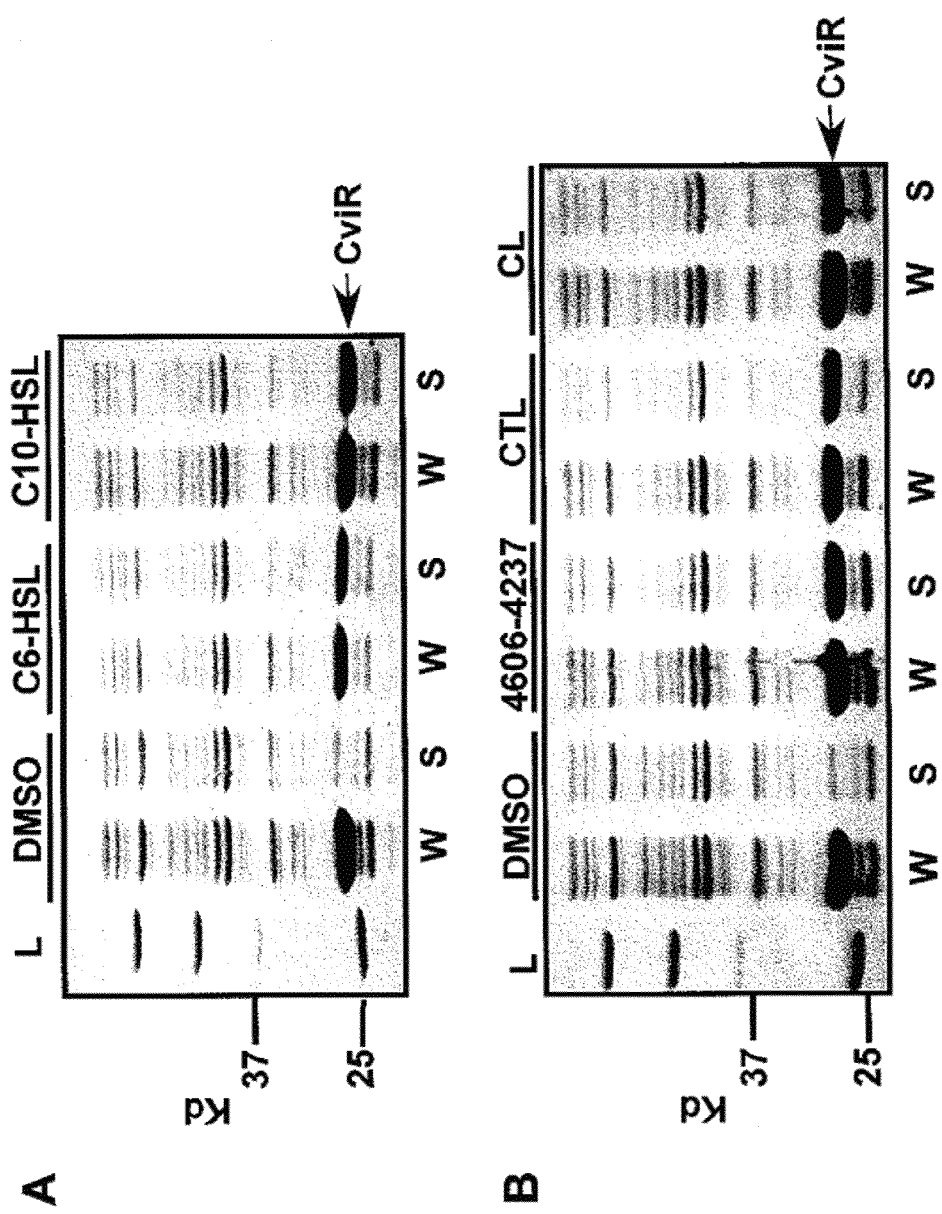
FIG. 4. Solubility Analysis of CviR Bound to Ligands. (A) SDS-PAGE analysis of *E. coli* whole cell (W) and soluble (S) extracts of cell cultures expressing CviR in the presence of dimethyl sulfoxide (DMSO) (Lanes 2 and 3), C6-HSL (Lanes 4 and 5), and C10-HSL (Lanes 6 and 7). (B) SDS-PAGE analysis of *E. coli* whole cell (W) and soluble (S) extracts of cell cultures expressing CviR in the presence of DMSO (Lanes 2 and 3), 4606-4237 (Lanes 4 and 5), Chloro-thiolactone (CTL) (Lanes 6 and 7) and Chlorolactone (CL) (Lanes 8 and 9). The L above the first lane designates the molecular weight ladder.

Similar to the paradigmatic TraR AHL binding protein from Agrobacterium tumefaciens, the experiments described herein showed that CviR is only soluble, and thus, only able to bind DNA and activate transcription when bound to its cognate AHL ligand (FIG. 4A DMSO control lanes). This finding engenders the question whether some of the antagonists function by interfering with CviR folding and solubility. The solubility characteristics of CviR were analyzed in the presence of the various molecules under study. To do this, CviR was expressed in E. coli in the presence of exogenously supplied C4-HSL, C6-HSL, C8-HSL, C10-HSL, C12-HSL, and C14-HSL, 4606-4237, CTL, and CL. As controls, the protein was also expressed in the absence of any AHL or antagonist. In each case, whole cell and soluble fractions of cell lysates were analyzed by SDS-PAGE to assess whether the CviR protein in question had been stabilized.

Figure 10:
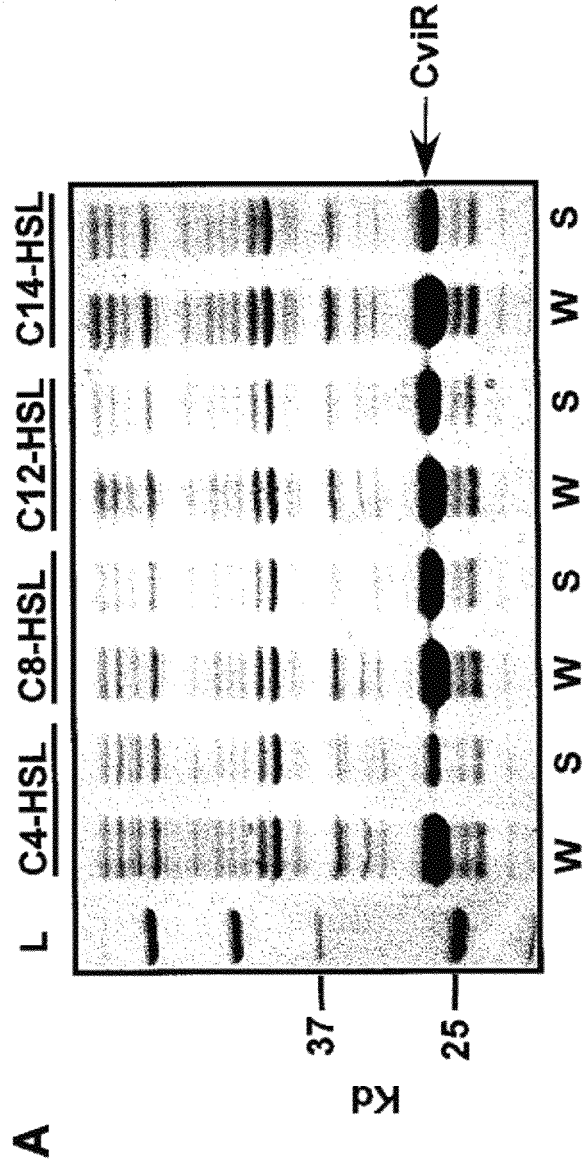
FIG. 10. Solubility Analysis of CviR. Protein solubility was assessed by SDS-PAGE analysis of *E. coli* whole cell (W) and soluble (S) extracts expressing CviR in the presence of C4-HSL (Lanes 2 and 3), C8-HSL (Lanes 4 and 5), C12-HSL (Lanes 6 and 7) and C14-HSL (Lanes 8 and 9). The L designates the molecular weight ladder.
Figure 11:
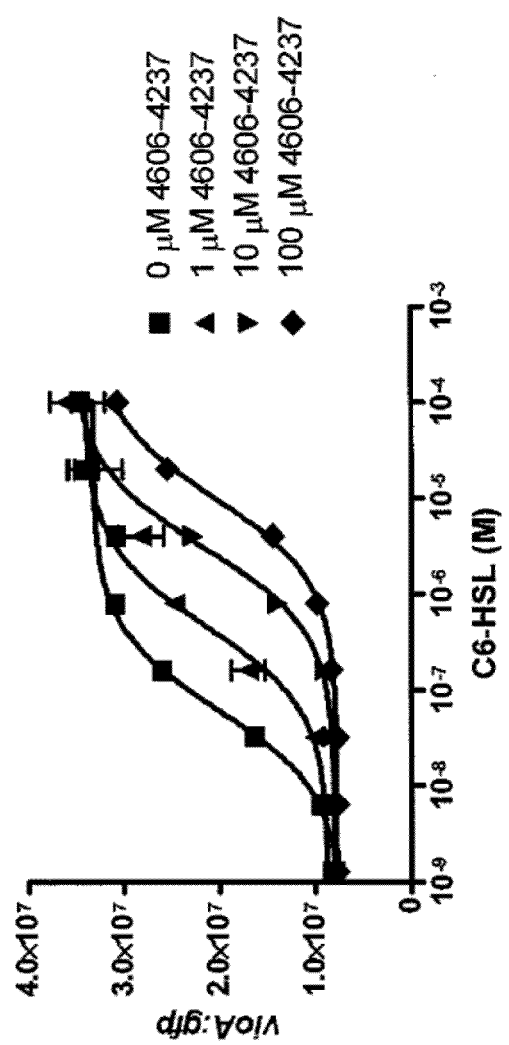
FIG. 11. C6-HSL and 4606-4237 Competition Assay. Activation of vioA:gfp expression was measured as a function of C6-HSL concentration at 0, 1, 10 and 100 µM concentration of 4606-4237. Error bars represent the standard error of the mean for three independent trials.
Figure 12:
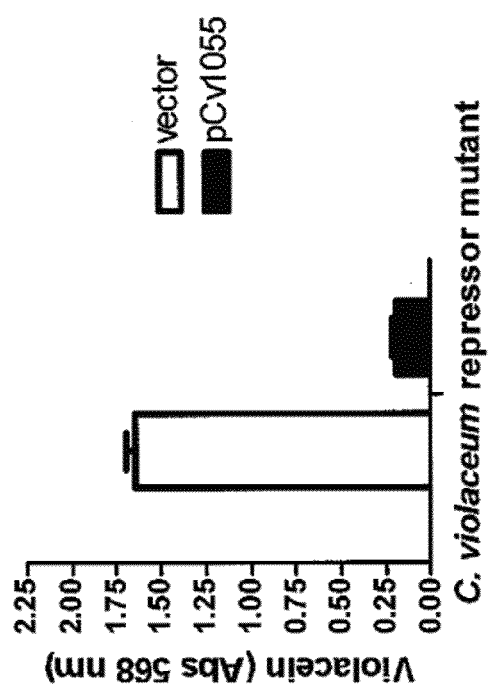
FIG. 12. Repression of Violacein Production by Gene CV1055. Violacein production was measured in a *C. violaceum* strain carrying a transposon insertion in gene cv1055 (this strain is called 31532P1). The assays were carried out with the strain carrying the empty vector, pJAK16 (black bars) or the vector gene CV1055 (white bars) encoding the putative violacein repressor. Cells were grown overnight in triplicate and the violacein pigment was methanol extracted and measured as function of absorbance at 568 nm.

The CviR protein was not soluble if no ligand was added (FIG. 4A, DMSO control lanes). By contrast, CviR became soluble when expressed in the presence of all the tested AHLs (C6-HSL and C10-HSL shown as representative in FIG. 4A, all others are shown in FIG. 10). The three synthetic antagonists, 4606-4237, CTL, and CL also promoted CviR31532 folding and solubility (FIG. 4B). These are surprising results because CviR is agonized by C4-HSL and C6-HSL, partially agonized by C8-HSL, but antagonized by C10-HSL, C12-HSL, C14-HSL, 4606-4237, CTL and CL (FIG. 3A-D). Therefore, we come to the conclusion that all of the CviR antagonist molecules (C10-HSL, C12-HSL, C14-HSL, 4606-4237, CTL, and CL) are bound by CviR, and thus do not antagonize the receptor by inhibiting protein folding and solubility.

Example 6

DNA Binding Analysis of CviR31532

To further investigate the mechanism underlying antagonism of the CviR receptor, an examination was undertaken of whether the soluble CviR antagonist complexes were incapable of binding DNA, and thus unable to activate transcription. The first step was purifying the CviR protein in complex with the native C6-HSL ligand, and in complex with C8-HSL, C10-HSL, C12-HSL and C14-HSL. The CviR protein was also purified in complex with each of the synthetic antagonist molecules, 4606-4237, CTL, and CL. Performance of DNA gel mobility shift analyses enabled assessment of the binding of each of these purified, loaded protein complexes to the vioA promoter. It was not possible to purify CviR in the presence of C4-HSL, which is consistent with the high $EC_{50}$ value and therefore, low affinity CviR has for this molecule (FIG. 3A).

Figure 5:
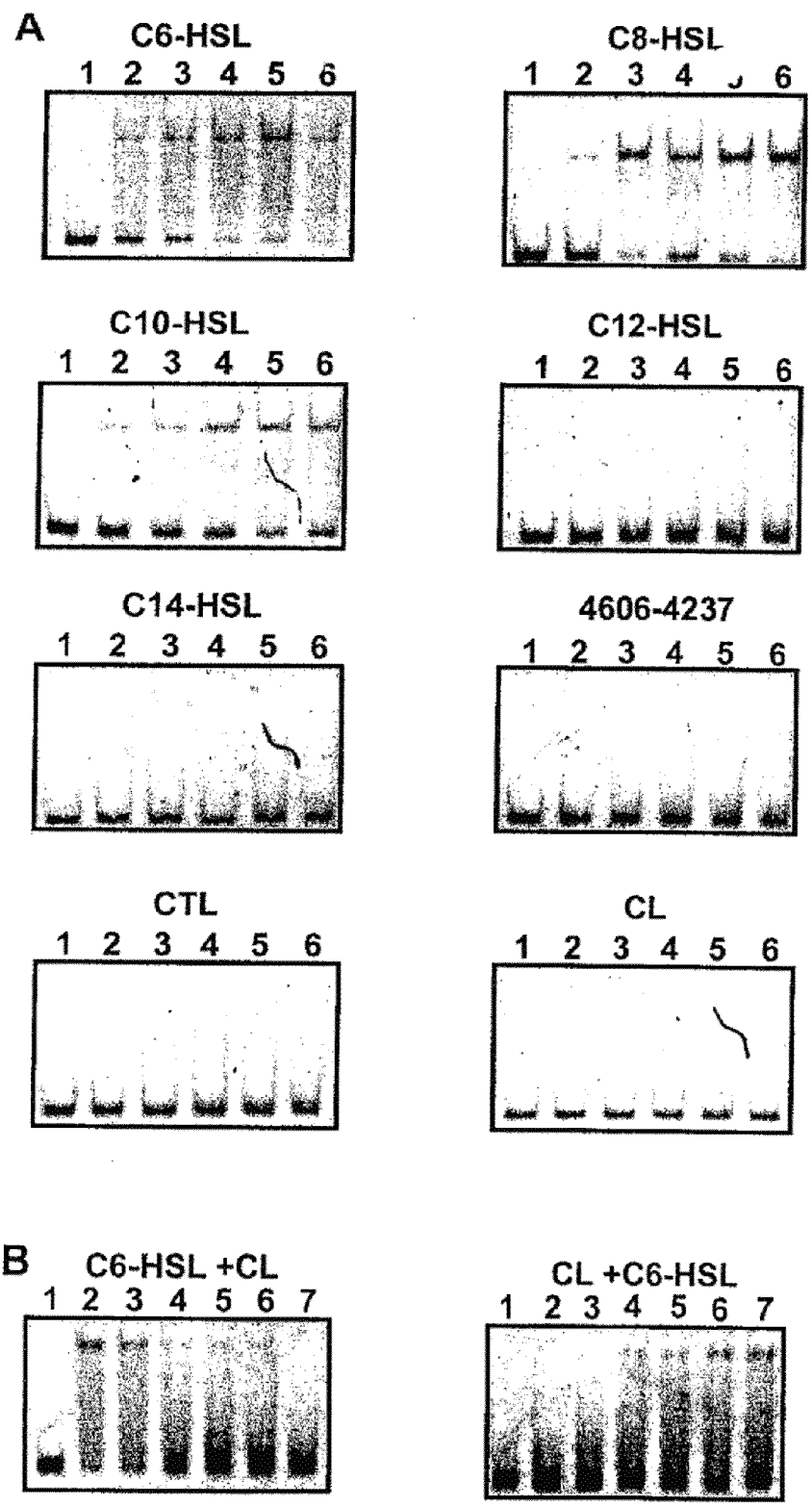
FIG. 5. Gel Mobility Shift Analysis of the CviR31532 Protein Bound to Agonist and Antagonist Molecules. (A) CviR binding to the vioA promoter at concentrations of 0 nM (Lane 1), 100 nM (Lane 2), 200 nM (Lane 3), 300 nM (Lane 4), 400 nM (Lane 5), and 500 nM (Lane 6). Each panel corresponds to CviR loaded with a different molecule. (B) CviR proteins loaded with C6-HSL and loaded with CL at concentrations of 500 nM were incubated for 20 min with 0, 0.5, 1, 3, 5 or 10 µM CL and C6-HSL, respectively. The vioA probe was subsequently added and allowed to incubate at room temperature for 20 additional min prior to being subjected to electrophoresis. No protein (Lane 1), 0 µM (Lane 2), 0.5 µM (Lane 3), 1 µM (Lane 4), 3 µM (Lane 5), 5 µM (Lane 6), 10 µM (Lane 7) CL or C6-HSL.

CviR loaded with its cognate C6-HSL signal molecule binds DNA with high affinity at even the lowest ligand concentration of 100 nM (FIG. 5A). CviR loaded with C6-HSL did not bind to a control DNA probe consisting of a 300 nucleotide region of the vioB open region frame (data not shown). CviR protein loaded with C8-HSL bound DNA with similar affinity to the C6-HSL loaded CviR complex (FIG. 5A). However, having shown previously that C8-HSL is incapable of activating maximal gfp expression (FIG. 3A), this indicates that CviR loaded with C8-HSL can bind DNA properly but the complex is in a conformation that is not fully competent as a transcriptional activator. Having shown that C10-HSL is an antagonist of the CviR protein (FIG. 3B), another surprising result was that C10-HSL, as well, does not abolish DNA binding of the CviR protein (FIG. 5A). This result indicates that C10-HSL locks CviR into a conformation incapable of productive interaction with RNA polymerase. Purified CviR bound to the remaining antagonist molecules: C12-HSL, C14-HSL, as well as the synthetic antagonists, 4606-4237, CTL, and CL displayed no ability to bind DNA (FIG. 5A). Therefore, this final set of molecules antagonize the CviR receptor by inhibiting DNA binding, rather than by inhibiting interaction with RNA polymerase.

To determine if CviR could reversibly bind C6-HSL, gel mobility shift analyses of CviR loaded with C6-HSL were performed in the presence of increasing concentrations of the most potent synthetic antagonist, CL (FIG. 5B). C6-HSL loaded CviR protein was incubated with the vioA probe at a concentration of 500 nM and the CL molecule was added at final concentrations of 0, 0.5, 1, 3, 5 and 10 µM. DNA binding decreased in a dose dependent manner with increasing concentrations of the CL antagonist, suggesting that the CL antagonist could exchange with the C6-HSL bound to the CviR protein. The reciprocal experiment tested whether C6-HSL could replace CL bound to CviR. In this experiment, CviR loaded with CL at a concentration of 500 nM was incubated in the presence of increasing concentrations of C6-HSL (from 0 to 10 µM). At a concentration of 1 µM C6-HSL, we could detect a modest shift of the DNA probe (FIG. 5B). This shift was dose dependent, with the strongest gel mobility shift observed at a concentration of 10 µM C6-HSL. These experiments show that when CL is exchanged for C6-HSL, the complex transitions from being fully capable of DNA binding to fully incapable of DNA binding (FIG. 5B, left panel). However, the gel shifts show that C6-HSL is not likewise capable of replacing CL to generate fully competent DNA bound complex (FIG. 5B, right panel). In this case, the protein must exchange the ligand and convert from a DNA-binding incompetent form to a DNA-binding competent form. Most likely, some of the protein misfolds during this process. Nonetheless, these analyses show that ligand binding is a reversible event because exchange can occur after CviR has folded around the native ligand or the synthetic antagonist molecule.

Example 7

Inhibition of the Membrane-Bound Quorum-Sensing Receptor, LuxN

Figure 1B:
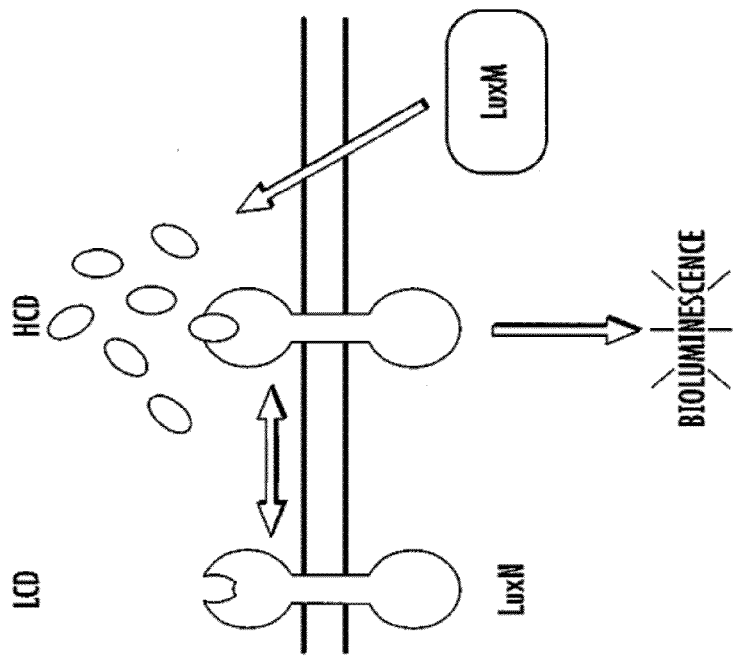
FIG. 1. The *C. violaceum* and *V. harveyi* Quorum-Sensing Circuits. (A) The cytoplasmic quorum-sensing receptor, CviR from *C. violaceum* binds to the AHL autoinducer (black ovals) at high cell density (HCD). The CviR-AHL complex binds to DNA and activates expression of the vio genes required for production of the purple pigment, violacein. CviI is the C6-HSL synthase. (B) The membrane-bound quorum-sensing receptor, LuxN from *V. harveyi* binds to the AHL autoinducer (black ovals) at high cell density (HCD) resulting in a phosphorylation cascade that activates expression of the lux genes required for bioluminescence. LuxM is the 3OH-C4-HSL autoinducer synthase.
Figure 1A:
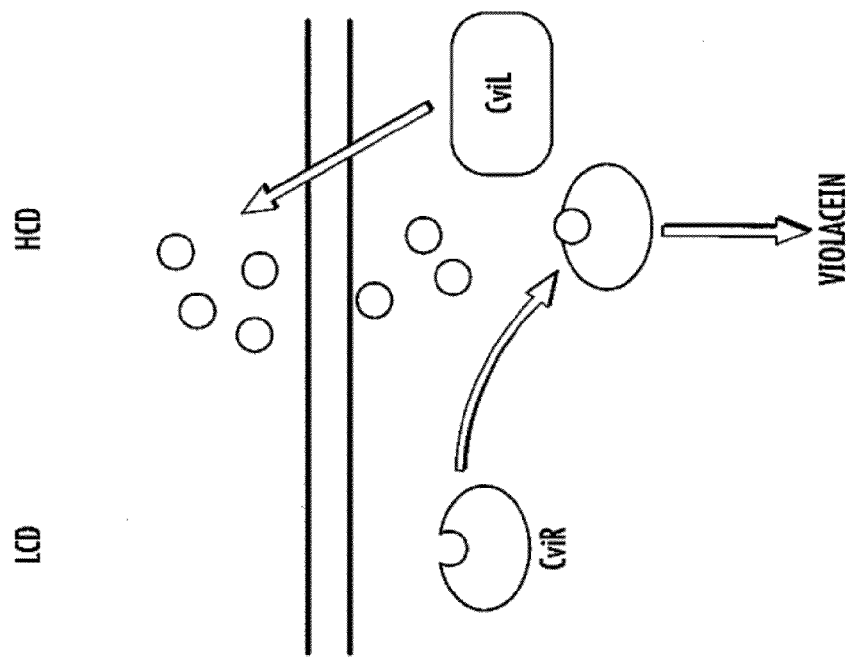

The experiments described above show that 4606-4237, CTL, and CL bind to the cytoplasmic CviR AHL receptor and act as potent antagonists. However, 4606-4237 was initially identified for its ability to interrupt AHL detection by the *V. harveyi* trans-membrane receptor LuxN (FIG. 1B). Thus, the experimental results described above engendered the question whether the dual inhibitory characteristic of 4606-4237 is a property exclusive to that molecule, or whether the other inhibitors, namely CTL and CL, might also be potent inhibitors of the LuxN receptor. If so, it would indicate that: (1) a rather generic AHL binding site exists in Gram-negative quorum-sensing receptors that recognize medium-chain length AHLs; (2) this binding site occurs irrespective of the receptor's overall domain architecture; and (3) the binding site is also independent of whether signal recognition occurs in the cytoplasm or in the periplasm.

To determine the properties of CTL and CL in relation to the LuxN receptor, the in vivo activity was examined of 4606-4237, CTL, and CL for *V. harveyi* LuxN using dose response analyses of the endogenous quorum-sensing-activated target, bioluminescence. Three different *V. harveyi* strains were examined (1) The wild type *V. harveyi* strain BB120 which has multiple quorum-sensing circuits, and thus responds to multiple autoinducers, only one of which is the AHL acting through LuxN. (2) *V. harveyi* BB960 which lacks the receptor for the second autoinducer making the AHL-LuxN circuit the dominant input into bioluminescence expression. (3) *V. harveyi* JMH624 which, in addition to lacking the receptor for the second autoinducer lacks the AHL synthase LuxM. Thus, *V. harveyi* JMH624 induces bioluminescence exclusively in response to the AHL, 3OH-C4-HSL signal but only when it is supplied exogenously. Exogenous addition of 20 nM 3OH-C4-HSL is sufficient to induce maximal bioluminescence in all of these strains. Importantly however, endogenously produced AHL accumulates to low micromolar levels in culture fluids of *V. harveyi* strains possessing the AHL synthase, LuxM.

Figure 6:
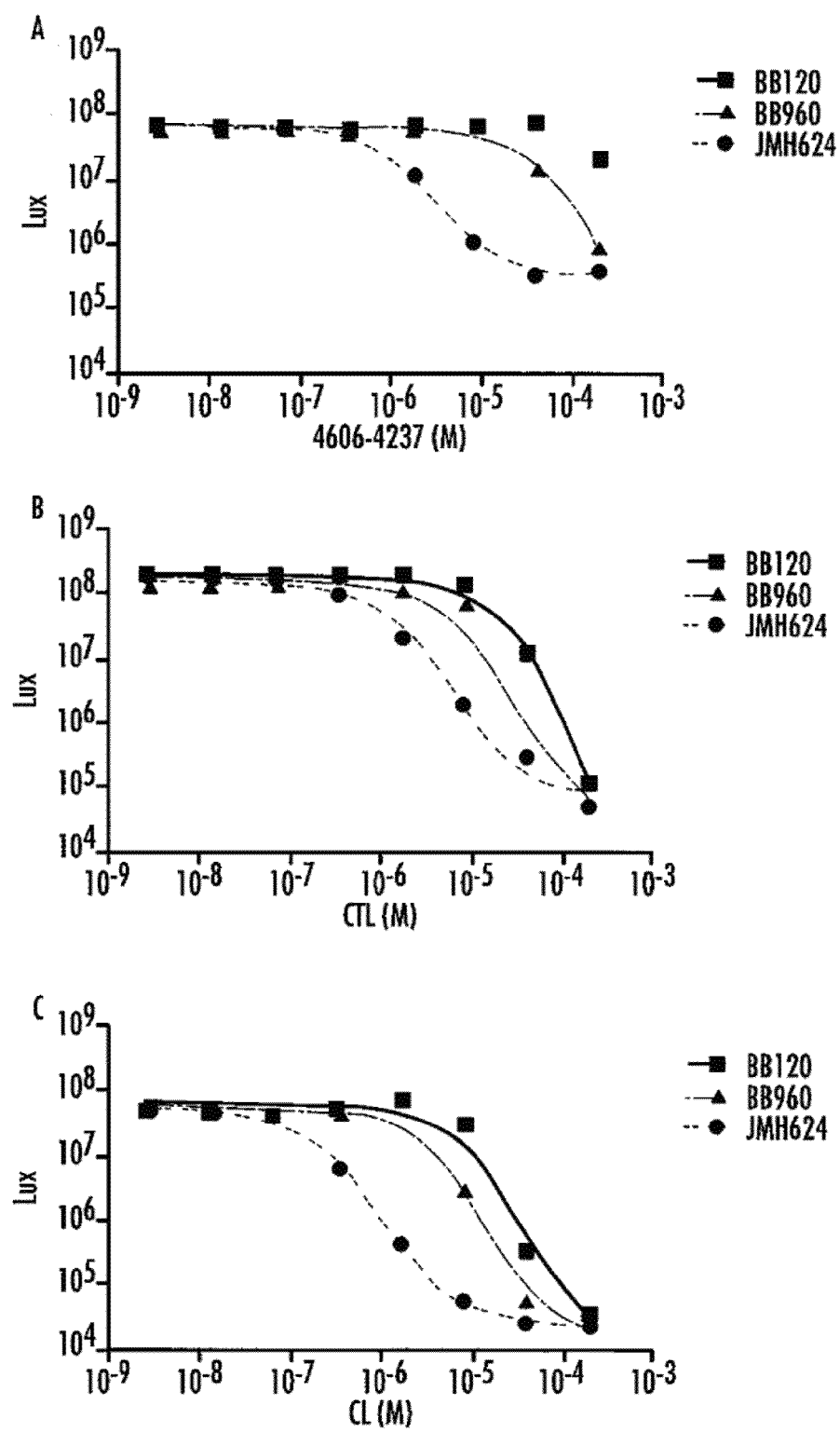
FIG. 6. *V. harveyi* Bioluminescence in Response to Antagonists. Light production from wild type *V. harveyi* (BB120), a luxPQ mutant (BB960), and a luxPQ, luxS double mutant (JMH624) was measured in the presence of the specified concentrations of 4606-4237 (A), CTL (B), or (CL) (C). Data were fit with a variable-slope sigmoidal dose-response curve to determine $IC_{50}$ values. Error bars although small are included and represent the standard error of the mean for three independent trials.

FIG. 6A shows that 4606-4237 does not inhibit bioluminescence in wild type *V. harveyi* (BB120; squares). However, in the absence of input from the second quorum-sensing system, modest inhibition occurs with an $IC_{50}$ value of 302 µM (BB960; triangles). One-hundred times stronger inhibition occurs in *V. harveyi* JMH624 in the presence of 20 nM 3OH-C4-HSL giving an $IC_{50}$ value of 3.0 µM (JMH624; circles). These results show that 4606-4237 is an antagonist of LuxN and can indeed inhibit LuxN-directed quorum sensing in *V. harveyi* but only if input from the second quorum-sensing circuit has first been eliminated or if the level of competing autoinducer signal present is reduced to a concentration significantly below that produced endogenously.

Unlike 4606-4237, the CTL molecule is capable of inhibiting all three *V. harveyi* strains; BB120, BB960, and JMH624+AHL with $IC_{50}$ values of 150 µM, 28 µM, and 6 µM, respectively (FIG. 6B). And, the CL molecule is the most potent LuxN antagonist, with $IC_{50}$ values for BB120, BB960, and JMH624+AHL of 40 µM, 14 µM, and 873 nM, respectively (FIG. 6C). Thus, the ability of these antagonist molecules to target LuxN parallels the results for the CviR receptor in terms of potency: CL>CTL>4606-4237. In the context of LuxN, alteration of 4606-4237 to CTL, or better to CL, makes the molecule able to interfere with AHL reception even in the face of a competing quorum-sensing system and in the presence of high levels of endogenously produced signal.

Example 8

*Chromobacterium violaceum* Infection of *Caenorhabditis elegans* is Quorum-Sensing-Dependent Quorum sensing in both Gram-negative and Gram-positive bacteria often controls processes critical for pathogenesis of eukaryotic hosts. *C. violaceum* is a human pathogen frequently infecting by means of introduction through lacerated skin. As a model system of *C. violaceum* infection of a eukaryotic host, infection of *C. elegans* was examined. Lifespan assays reveal that *C. violaceum* rapidly kills *C.*

*elegans*, with a median survival of the nematode of two days in the presence of *C. violaceum* compared to a median survival of fifteen days when grown in the presence of the non-pathogenic *E. coli* strain, OP50 (data not shown). A *C. violaceum* vioA mutant that is incapable of producing the violacein pigment remains fully capable of shortening *C. elegans* lifespan, showing that violacein is not responsible for *C. violaceum*-mediated killing of the nematode (data not shown).

To test if quorum sensing is required for *C. violaceum* killing of *C. elegans*, lifespan assays were performed with the *C. violaceum* cviI mutant that makes no AHL signal and thus does not express quorum-sensing-dependent genes. In the presence of the mutant strain, the median *C. elegans* lifespan is twelve days (FIG. 7A; DMSO control). Exogenous addition of the native autoinducer molecule, C6-HSL restored quorum sensing and complemented the cviI mutant's ability to kill *C. elegans* (median lifespan=4 days, FIG. 7A). This result provides strong evidence that a factor(s) other than violacein that is under quorum-sensing control is responsible for *C. violaceum* pathogenicity of *C. elegans*.

Figure 7:
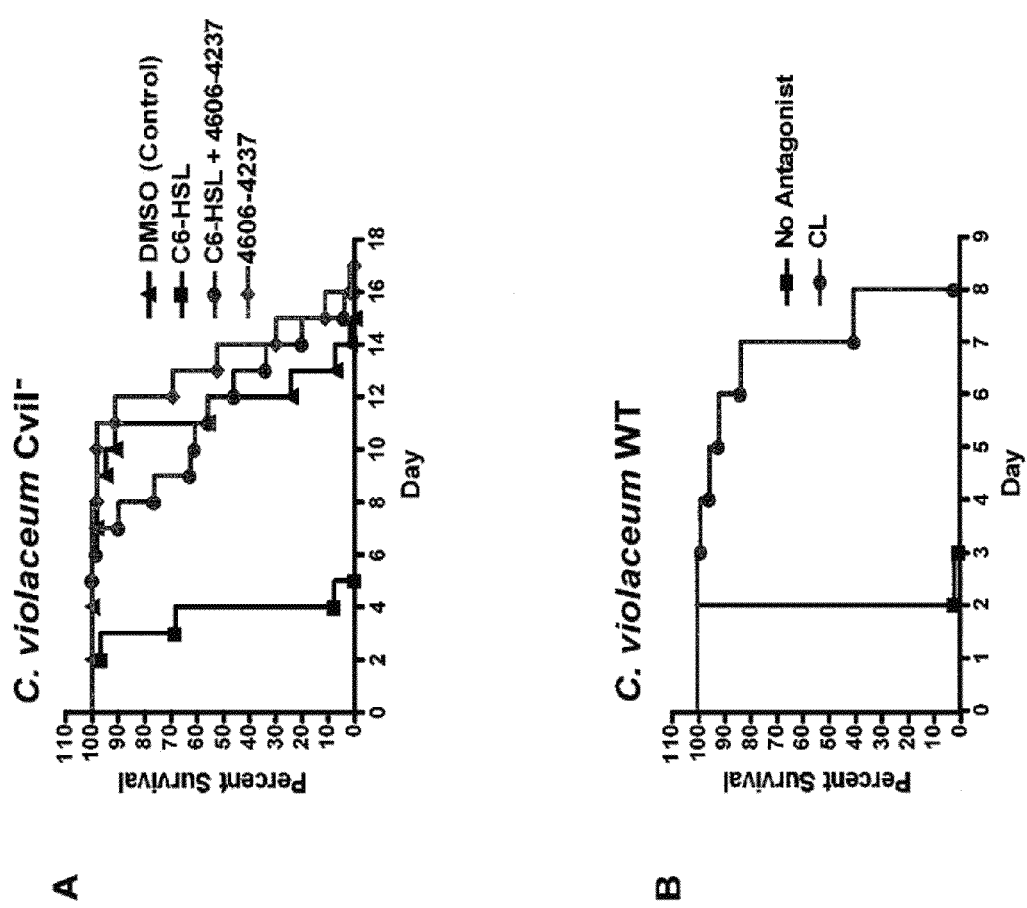
FIG. 7. *C. elegans* Survival Following *C. violaceum* Infection and Treatment. (A) Kaplan-Meier survival curve of a *C. elegans* population infected with *C. violaceum* cviI mutant in the presence of the control solution of dimethyl sulfoxide (DMSO) or the specified molecules. (B) Kaplan-Meier survival curve of a *C. elegans* population infected with wild type *C. violaceum* in the absence of any quorum-sensing antagonist or in the presence of CL.

This assay system also facilitated a test as to whether the 4606-4237 antagonist could inhibit quorum-sensing-mediated killing of the nematode by *C. violaceum*. Indeed, the simultaneous addition of C6-HSL and 4606-4237 to the cviI mutant increased *C. elegans* median survival to twelve days (FIG. 7A). The 4606-4237 molecule had little affect on *C. elegans* when added to the cviI *C. violaceum* mutant in the absence of the C6-HSL signal (FIG. 7A).

With the ultimate goal of control of virulent processes of fully infective wild type bacteria, a test was conducted of the extremely potent antagonist CL, on wild type *C. violaceum*; i.e., a *C. violaceum* strain that is fully capable of producing and responding to C6-HSL signal. At a concentration of only 20 µM, CL protected *C. elegans* from killing by wild type *C. violaceum* (FIG. 7B). In this context, *C. elegans* lifespan increased from two days to seven days. Thus, the lead quorum-sensing antagonist discovered in this work is capable of specifically disrupting quorum-sensing-directed pathogenicity in a wild type bacterium and, in so doing, improve the outcome of a nematode animal host in the model system.

Example 9

Treatment of Bacterial Infection Associated with Burns

Described herein is the use of mice, *Mus musculus*, as an animal burn infection model to determine the stability and efficacy of the experimental compounds in treating vertebrate infections of burn wounds. The mouse burn infection model is well established in the scientific literature for the bacterium *P. aeruginosa*. Many variations of this method have been developed for other virulent bacteria that often cause skin infections.

The protocol described in this example is a variation of the original burned-mouse model by Stieritz and Holder (1975), using a water scald method to thermally injure the mice rather than the original ethanol burn method (Rumbaugh et al. 1999). Swiss Webster adult female mice, weighing between 20 and 24 grams are used. The mice are anesthetized with intraperitoneal injection of 0.4 ml of 5% sodium pentobarbital solution. The back of the mouse is shaved and the mouse is placed into a plastic template that contains a 4.5 by 1.8 cm opening, which is positioned over the shaved back. The exposed surface of the back is placed in 90° C. water for 10 seconds. This induces a full thickness burn on the back of the mouse, resulting in a burn area that encompasses approximately 15% of the entire surface area of the mouse. The burn area is immediately rehydrated by subcutaneous injection of 0.8 ml of sterile 0.9% NaCl solution. As controls, one group of animals is shaved on the back of the mouse, anesthetized and placed into the plastic template, but is not thermally injured.

The thermally injured mice are divided into four subgroups: non-infected, non-infected/treated, infected, and infected/treated. The infected animals are challenged with 100 µL of inocula of either *C. violaceum* or *P. aeruginosa* suspended in phosphate buffered saline and administered topically or injected subcutaneously at the anterior edge of the wound. The non-infected animals receive a 100 µL dose of phosphate buffered saline administered topically or injected subcutaneously. The compounds tested for quorum sensing inhibition are individually injected subcutaneously at the wound site or applied topically as an ointment. In another variation, combinations of the compounds are administered. The quorum sensing inhibitors are administered at regular intervals (e.g., every 4 hours).

Generally, bacterial virulence is measured by an endpoint assay, however, an alternative method is as follows. The mice are euthanized at 24 hours post burn. Skin sections of 5 by 5 mm are obtained from the burn area of all groups. The heart, liver, and spleen are obtained to determine the bacterial load associated with each tissue sample. The $LD_{50}$ for *C. violaceum* inocula in mice is determined. To do this, serial dilutions of *C. violaceum* are plated on agar petri-plates to determine the colony forming units in each dilution. Five mice are infected as described above for each *C. violaceum* dilution. Onset of infection is monitored and infected animals are immediately euthanized. The $LD_{50}$ of *P. aeruginosa* is less than 10 colony forming units. To evaluate the general toxicity of the quorum sensing inhibitors, the $LD_{50}$ of the compounds is determined by administering the compounds as described in the protocol.

CITED REFERENCES

Bassler, B. L., Wright, M., Showalter, R. E., and Silverman, M. R. (1993). Intercellular signaling in *Vibrio harveyi*: sequence and function of genes regulating expression of luminescence. Mol. Microbiol. 9, 773-786.

Bassler, B. L., Wright, M., and Silverman, M. R. (1994). Multiple signalling systems controlling expression of luminescence in *Vibrio harveyi*: sequence and function of genes encoding a second sensory pathway. Mol Microbiol 13, 273-286.

Freeman, J. A., Lilley, B. N., and Bassler, B. L. (2000). A genetic analysis of the functions of LuxN: a two-component hybrid sensor kinase that regulates quorum sensing in *Vibrio harveyi*. Mol Microbiol 35, 139-149.

Fuqua, W. C., Winans, S. C., and Greenberg, E. P. (1994). Quorum sensing in bacteria: the LuxR-LuxI family of cell density-responsive transcriptional regulators. J Bacteriol 176, 269-275.

Furste, J. P., Pansegrau, W., Frank, R., Blocker, H., Scholz, P., Bagdasarian, M., and Lanka, E. (1986). Molecular cloning of the plasmid RP4 primase region in a multi-host-range tacP expression vector. Gene 48, 119-131.

Jung, K., Odenbach, T., and Timmen, M. (2007). The quorum-sensing hybrid histidine kinase LuxN of *Vibrio harveyi* contains a periplasmically located N terminus J Bacteriol 189, 2945-2948.

Minogue, T. D., Wehland-von Trebra, M., Bernhard, F., and von Bodman, S. B. (2002). The autoregulatory role of EsaR, a quorum-sensing regulator in *Pantoea stewartii* ssp. *stewartii*: evidence for a repressor function. Mol Microbiol 44, 1625-1635.

Minogue, T. D., Carlier, A. L., Koutsoudis, M. D., and von Bodman, S. B. (2005). The cell density-dependent expression of stewartan exopolysaccharide in *Pantoea stewartii* ssp. *stewartii* is a function of EsaR-mediated repression of the rcsA gene. Mol Microbiol 56, 189-203.

Rumbaugh et al. (1999) Contribution of quorum sensing to the virulence of *Pseudomonas aeruginosa* in burn wound infections. *Infect Immun.* 67, 5854-62.

Sjoblom, S., Brader, G., Koch, G., and Palva, E. T. (2006). Cooperation of two distinct ExpR regulators controls quorum sensing specificity and virulence in the plant pathogen *Erwinia carotovora*. Mol Microbiol 60, 1474-1489.

Stieritz and Holder (1975). Experimental studies of the pathogenesis of infections due to *Pseudomonas aeruginosa*: description of a burned mouse model. *J infect Dis.* 131, 688-91.

Swem, L. R., Swem, D. L., Wingreen, N. S., and Bassler, B. L. (2008). Deducing receptor signaling parameters from in vivo analysis: LuxN/AI-1 quorum sensing in *Vibrio harveyi*. Cell 134, 461-473.

Throup, J., M. K. Winson, N. J. Bainton, B. W. Bycroft, P. Williams, & G. S. A. B. Stewart (1995). Signalling in bacteria beyond bioluminescence. In Bioluminescence and Chemiluminescence: Fundamentals and Applied Aspects, L. K. A. Campbell, & P. Stanley, ed. (Chichester: Wiley), pp. 89-92.

Timmen, M., Bassler, B. L., and Jung, K. (2006). AI-1 influences the kinase activity but not the phosphatase activity of LuxN of *Vibrio harveyi*. J Biol Chem 281, 24398-24404.

Zhang, R. G., Pappas, T., Brace, J. L., Miller, P. C., Oulmassov, T., Molyneaux, J. M., Anderson, J. C., Bashkin, J. K., Winans, S. C., and Joachimiak, A. (2002). Structure of a bacterial quorum-sensing transcription factor complexed with pheromone and DNA. Nature 417, 971-974.

Zhu, J., and Winans, S. C. (1999). Autoinducer binding by the quorum-sensing regulator TraR increases affinity for target promoters in vitro and decreases TraR turnover rates in whole cells. Proc Natl Acad Sci USA 96, 4832-4837.

Zhu, J., and Winans, S. C. (2001). The quorum-sensing transcriptional regulator TraR requires its cognate signaling ligand for protein folding, protease resistance, and dimerization. Proc Natl Acad Sci USA 98, 1507-1512.

What is claimed is:

1. A small molecule analog of 4-(4-chloro-2-methylphenoxy)-N-(2-oxotetrahydrothiophen-3-yl)butanamide wherein said small molecule is represented by the formula:

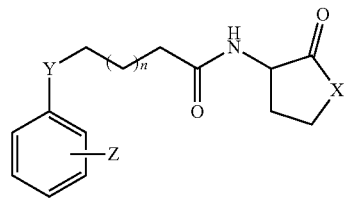

wherein X is O or S; n is 0, 1 or 2; Y is O, S or $CH_2$; and Z is a halogen, hydroxyl, alkoxyl, cyano, nitro, amido, acetamido, amino, alkylamino, aryl, heteroaryl, acyl, alkyl, cycloalkyl, sulfonamide, alkyl sulfonamide or a combination thereof; and wherein Z is located at the ortho, meta or para position or at a combination thereof.

2. The molecule of claim 1 that is

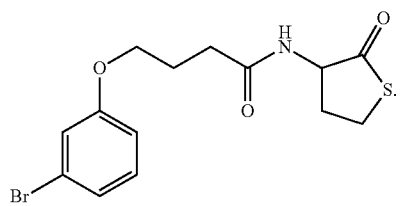 [SMILES: O=C(CCCOc1cccc(Br)c1)NC1CCSC1=O]

3. The molecule of claim 1 that is CTL.
4. The molecule of claim 1 that is CL.
5. The molecule of claim 1 that is o-fluoro-chloro-lactone.
6. The molecule of claim 1 that is m-fluoro-chloro-lactone.
7. A method of controlling growth of quorum-sensing bacteria attached to a solid surface comprising exposing the bacteria to a bacterial biofilm-inhibiting composition comprising the molecule of claim 2.
8. A method of preventing biofilm formation on a solid surface comprising administering to the surface a bacterial biofilm-inhibiting composition comprising the molecule of claim 2.
9. A method of inhibiting quorum sensing-mediated activity in bacteria comprising contacting the bacteria with the molecule of claim 2, wherein the activity is production of virulence factors.
10. The method of claim 9 wherein the bacterial species is selected from the group consisting of *V. harveyi, C. violaceum* and *P. aeruginosa*.

* * * * *